United States Patent [19]

Kamen et al.

[11] 4,219,721
[45] Aug. 26, 1980

[54] MARKING OF LENSES

[75] Inventors: Melvin E. Kamen, Woodcliff Lake, N.J.; Morris Bernfeld, Long Island City, N.Y.; John C. Pelc, Richmond, Va.

[73] Assignee: Revlon, Inc., New York, N.Y.

[21] Appl. No.: 936,082

[22] Filed: Aug. 23, 1978

[51] Int. Cl.² ............................................. B23K 27/00
[52] U.S. Cl. ...................... 219/121 LM; 269/321 W
[58] Field of Search .................. 219/121 L, 121 LM; 351/160, 51, 19–22; 350/1.2, 1.3, 1.4; 269/321 R, 321 W

[56] References Cited

U.S. PATENT DOCUMENTS

| | | | |
|---|---|---|---|
| 2,133,498 | 10/1938 | Dittmer | 351/160 |
| 3,527,198 | 9/1970 | Takaoka | 219/121 LM |
| 3,549,733 | 12/1970 | Caddell | 219/121 LM |
| 3,627,858 | 12/1971 | Parts et al. | 219/121 LM |
| 3,663,793 | 5/1972 | Petro et al. | 219/121 LM |
| 3,833,786 | 9/1974 | Brucker | 219/121 L |
| 4,032,861 | 6/1977 | Rothrock | 219/121 L |
| 4,039,827 | 8/1977 | Zdrok et al. | 250/271 |
| 4,148,548 | 4/1979 | Thompson | 350/1.3 |

OTHER PUBLICATIONS

Obrig et al., Contact Lenses, 3rd edition, p. 330, 1957.

*Primary Examiner*—C. L. Albritton
*Attorney, Agent, or Firm*—Leon E. Tenenbaum

[57] ABSTRACT

A laser beam is used to provide rapid, clear and permanent marking of plastic lenses.

1 Claim, 4 Drawing Figures

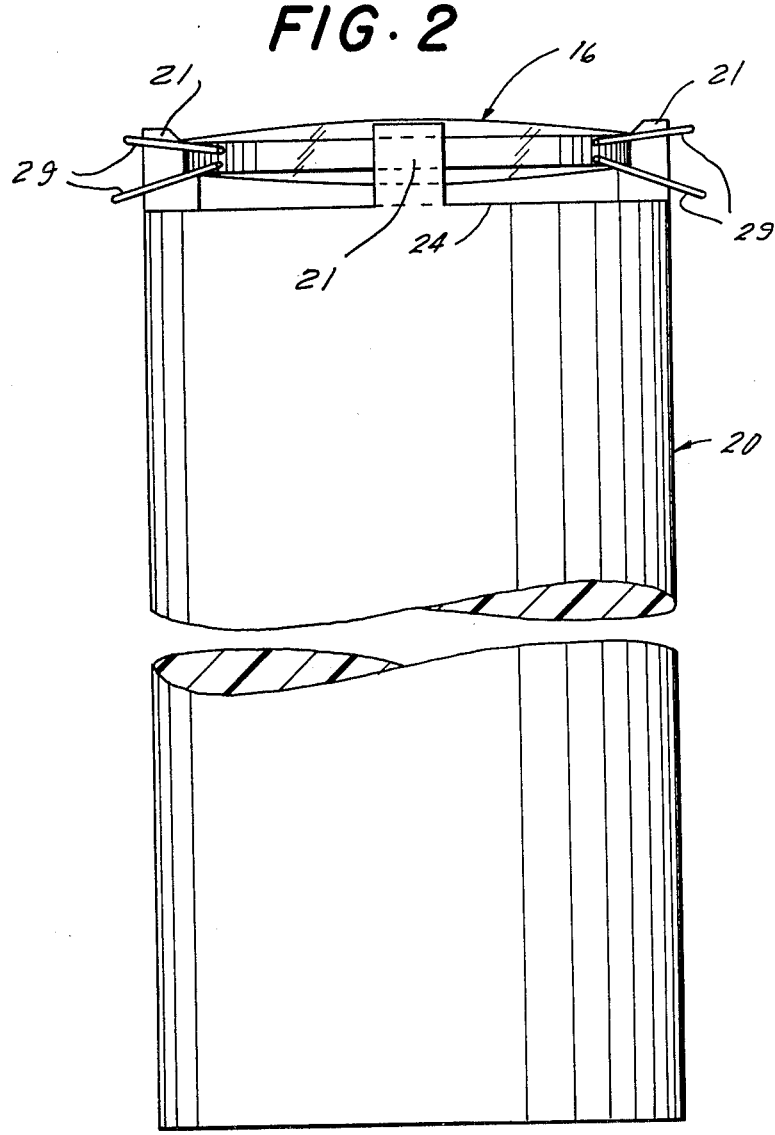

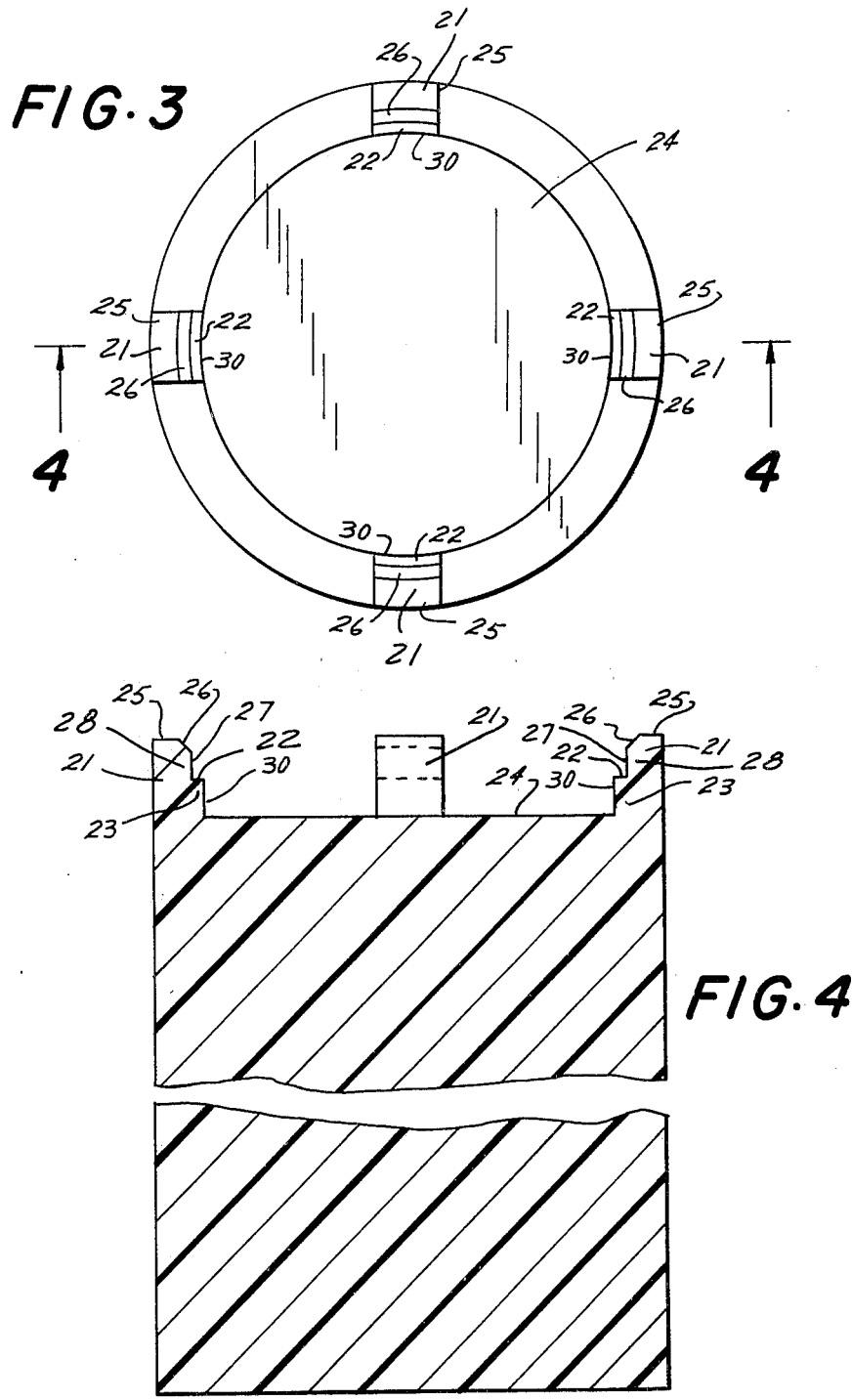

MARKING OF LENSES

The present invention relates to the marking of lenses. It particularly relates to the marking of plastic lenses, such as, for example, intraocular plastic lenses, composed of polymeric methacrylates.

It is often necessary to mark plastic intraocular lenses with a special reference number or code to establish permanent records thereon. The application of such number or code to a lens has presented numerous problems.

The prior art used painting, leaching or mechanical engraving of the plastic lens to identify the lens with letters, numbers, symbols or a combination of all. These methods leave much to be desired. The painting or leaching of the plastic may cause crazing, cracking or chemical changes or leave an undesirable residue. The mechanical engraving method becomes exceedingly difficult when working with objects as small as intraocular lenses, and having to confine the mechanical engraving to a minute area of such lenses. In addition, the mechanical engraving creates rough edges and rough surfaces in which body fluids may collect and act as a harbour for potentially dangerous micro-organisms when the lens is in the eye. All the above methods are very exacting, tedious and time-consuming.

U.S. Pat. No. 4,039,827 discloses a method of marking plastic intraocular lenses using ultra-violet radiation in the electromagnetic range of about 2537 angstroms. This method requires an exposure time of about 10 minutes to bring about a change in the refractive index of the lens material so that the marking could be read.

It is an object of the present invention to provide a method for marking plastic lenses without the use of chemicals which may leave residues on or cause damage to the lens.

It is a further object of the present invention to provide a method for marking plastic lenses which avoids the use of mechanical contact as a means for marking the lens.

It is another object of the present invention to provide a rapid method for marking plastic lenses.

It is still another object of the present invention to provide a method for securing the plastic lens in place during the marking operation.

In accordance with the present invention plastic lenses are marked with desired characters by exposing the surface of the lens to a laser beam which has been passed through a mask or stencil, said mask or stencil being provided with a configuration in the shape of the desired character, permitting the passage therethrough of the laser beam. Exposure of the plastic lens to the laser beam vaporizes the plastic of the exposed portions of the lens into the configuration present in the mask or stencil.

Details of the invention will become more readily apparent from the following description when taken in conjunction with the accompanying drawings in which:

FIG. 2 is a perspective view of a holder for securing the plastic lens in place during the marking operation and the lens held therein.

FIG. 3 is a top plan view of the holder.

FIG. 4 is a sectional view of the holder along the lines 4—4 of FIG. 3.

Figure 1:
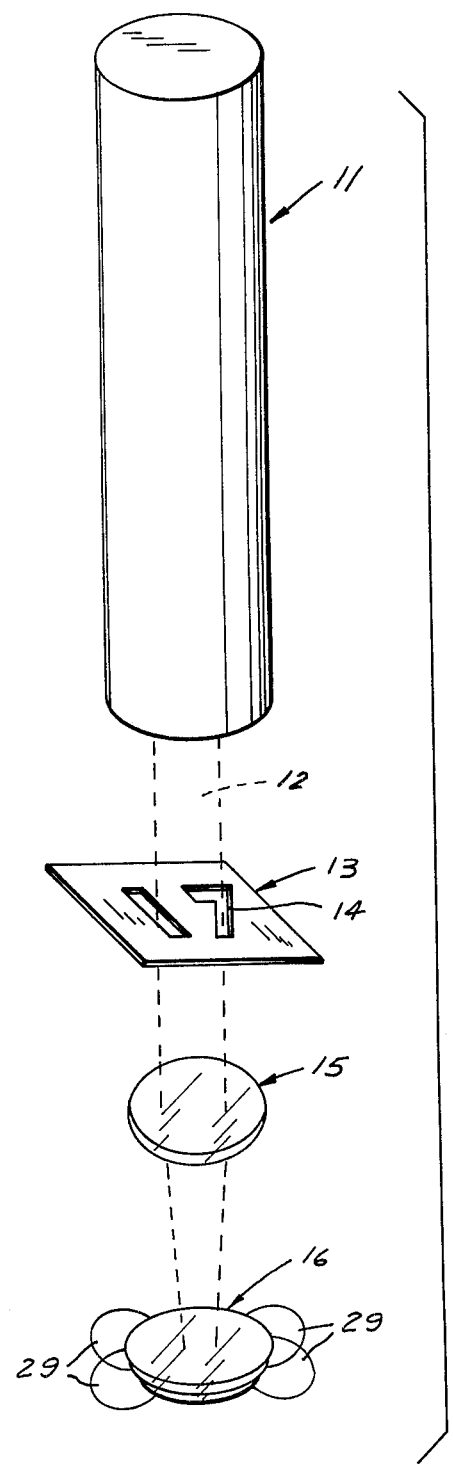
FIG. 1 is a diagrammatic view of the arrangement of the laser mask and lens.

Referring to FIG. 1 the source 11 of the laser beam 12 is a Lasermark #901 Laser system manufactured by the Lasermark division of Lumonics Research Ltd. of Ontario, Canada. The beam passes through a mask or stencil 13 having openings 14 permitting the passage therethrough of the laser beam. The mask is constructed of any metal impervious to laser beams. Suitable metals include gold, silver, copper, aluminum, brass, beryllium, and the like. A preferred material is a copper-beryllium alloy, #25 beryllium-copper alloy. After passing through the mask the rays enter a focussing lens 15 which focusses the beams onto the plastic lens 16. The focussing lens is constructed of a material which will transmit infrared radiation in the 10.6 micron range. Suitable materials for this purpose are germanium arsenide, gallium arsenide, cadmium telluride, and zinc selenide.

The plastic lens, which may be an intraocular plastic lens, is kept in place in a cylindrical holder 20. The holder is provided with a plurality of upwardly projecting prongs 21, preferably three or four prongs. The prongs are provided with inner ledges 22 upon which the plastic lens rests. These ledges are set at a predetermined height 23 above the top surface 24 of holder.

Preferably the top 25 of the prong is slanted or given a radius 26 from the inner face 27 of the wall 28 above the ledge to avoid the danger of scratching when the lens is removed from the holder. In the types of intraocular plastic lenses which have protruding loops for securing the lens in the eye, the loops 29 are placed outside the holder or as near to the outer edge of the holder to avoid interference with the marking.

The holder is constructed of a material having an extremely low coefficient of friction such as a highly polished metal like stainless steel, chrome or aluminum or a metal coated with plastic or a plastic such as Nylon. This minimizes any danger from abrasion or scratching.

The holder may be of any desired size depending upon the size of the lens being secured therein. The diameter of the lens will govern the distances between the inner faces 27 of the prongs and the thickness of the lens will determine the height of the prongs. Some tolerance is provided so that the lens can be readily removed. For example, if the lens has a diameter of 0.199" the distance between the inner faces of the opposed prongs is 0.201".

The source of the laser beam, the mask and the focussing lens can be arranged at any desired angle or direction to mark the plastic lens just where desired. The depth of the mark can be controlled by varying the intensity of the laser beam and/or the duration of exposure. With a beam having an intensity of about ⅝ Joule per square centimeter and an exposure of time of about one millionth of a second, a legible mark having a depth of about 0.012 with a resolution of about 0.002 inches can be produced. Resolution is defined as the spacing needed to make the mark legible. For example, in the case of the numeral 17 etched on the lens, the space between each digit is at least 0.002 inches and width of the face of each digit is 0.002 inches. The method thus provides marking in an extremely short time and lends itself to the rapid marking of a large number of lenses by using a rotary or linear conveyor to move the lenses in their holders under the laser beam.

Using the method of the present invention provides a clear, smooth mark on the lens without any rough edges.

We claim:

1. In a method for marking plastic lenses composed of polymethyl methacrylate which comprises:
    passing a laser beam through a mask having selected openings permitting the passage of the beam, said mask being composed of a material impervious to laser beams, and
    passing the selected laser beam through a focussing lens to focus said beam onto the plastic lens retained in a holder, said focussing lens being composed of material which will trasmit infrared radiation in the 10.6 micron range, the improvement wherein said plastic lens is held in a holder comprising a cylindrical body portion and a plurality of prongs extending upwardly therefrom, each prong having an inner ledge set at a predetermined height above the top surface of the body portion, and an upwardly projecting wall beyond the ledge, said wall being slanted outwardly to the top portion of the prong.

* * * * *